United States Patent
Sakamoto et al.

(10) Patent No.: US 6,951,944 B2
(45) Date of Patent: Oct. 4, 2005

(54) PRODUCTION OF IMIDAZOLE DERIVATIVES AND NOVEL INTERMEDIATES OF THE DERIVATIVES

(75) Inventors: Yasuhiko Sakamoto, Habikino (JP); Takushi Kurihara, Sakai (JP); Shinya Harusawa, Ibaraki (JP)

(73) Assignee: Azwell Inc., Osaka-Fu (JP)

( * ) Notice: Subject to any disclaimer, the term of this patent is extended or adjusted under 35 U.S.C. 154(b) by 0 days.

(21) Appl. No.: 10/501,801

(22) PCT Filed: Feb. 18, 2003

(86) PCT No.: PCT/JP03/01687

§ 371 (c)(1),
(2), (4) Date: Jul. 20, 2004

(87) PCT Pub. No.: WO03/070722

PCT Pub. Date: Aug. 28, 2003

(65) Prior Publication Data

US 2005/0043277 A1 Feb. 24, 2005

(30) Foreign Application Priority Data

Feb. 21, 2002 (JP) .......................... 2002-44760

(51) Int. Cl.[7] ...................... C07D 401/06; C07F 9/6506
(52) U.S. Cl. ....................................... 548/112
(58) Field of Search ......................... 548/112

(56) References Cited

U.S. PATENT DOCUMENTS 6,100,264 A  8/2000  Aloup et al.

FOREIGN PATENT DOCUMENTS

WO   93/12107   6/1993
WO   95/06037   3/1995

OTHER PUBLICATIONS

Synthesis (1988); No. 9: 735–739.
Vollinga et al., "A New Potent and Selective Histamine $H_3$ Receptor Agnoist, 4-(1H-Imidazol-4-ylmethyl)piperidine", Journal of Medicinal Chemistry (1994); 37: 332–333.
Harusawa et al., "An Efficient and Convenient Synthesis of 4-Vinylimidazoles Using Novel Homer–Wadsworth–Emmons (HWE) Reagent: Synthetic Studies Toward Novel Histamine $H_3$–Ligands", Synthesis (2002); No. 8: 1072–1078.

*Primary Examiner*—Kamal A. Saeed
(74) *Attorney, Agent, or Firm*—Hamre, Schumann, Mueller & Larson, P.C.

(57) ABSTRACT

An improvement in the production of imidazole derivatives including histamine $H_3$ agonist immepip and histamine $H_3$ antagonist VUF4929. Desired imidazole derivatives can be easily obtained in high yield by using novel intermediates represented by the general formula (I): (I) wherein $R^1$ is an amino-protecting group; $R^2$ and $R^3$ are each independently hydrogen, lower alkyl, or hydroxylated lower alkyl; $R^4$ is lower alkyl, halogenated lower alkyl, or substituted or unsubstituted phenyl; and A is $C_{1-3}$ alkylene

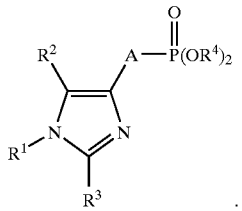

(I)

4 Claims, No Drawings

PRODUCTION OF IMIDAZOLE DERIVATIVES AND NOVEL INTERMEDIATES OF THE DERIVATIVES

TECHNICAL FIELD

The present invention relates to an improvement in the production of imidazole derivatives that are useful as histamine $H_3$ ligands, and novel intermediates thereof, more particularly, an improvement in the production of 4-(1H-imidazol-4-ylalkyl)piperidines, which are known as histamine $H_3$ agonists or antagonists, and novel intermediates thereof that are useful for the production of the imidazole derivatives.

BACKGROUND ART

It is known that 4-(1H-imidazol-4-ylmethyl)piperidine (nonproprietary name: immepip) has histamine $H_3$ agonistic activity and it is useful as histamine $H_3$-positive control reagent, and also is commercially available. Additionally, it is known that 4-(1H-imidazol-4-ylethyl)piperidine (known as VUF4929) has histamine $H_3$ antagonistic activity.

A process for manufacturing these imidazole derivatives is known, which comprises reacting 5-lithio salt of 1,2-di-protected-imidazole (e.g. 2-trimethylsilyl-N,N-dimethyl-1H-imidazole sulfonamide) with 4-pyridine-carbaldehyde to introduce a pyridin-4-ylhydroxymethyl group onto the 5-position of the imidazole nucleus, acetylating the hydroxyl group thereof, reducing it under a high pressure, and then deprotecting it (R. C. Vollinga, et al., J. Med. Chem. 37, 332–333, 1994 and WO 9506037).

However, this process has some disadvantages, such that it needs multiple reaction steps, and needs long reaction time under a high pressure in the reducing reaction, and so on. Additionally, it is a problem that the overall yield is very low, only 20% from the starting imidazole compound.

Alternatively, there is also known a process which includes reaction of imidazol-4-ylmethyl chlorides with the Grignard reagents prepared from N-protected-4-chloro-piperidine in the presence of a cupper salt, and then deprotection of the reaction product (WO 9312107). However, this process has problems, such that it needs to use a lot of heavy metals, and so forth.

Accordingly, it is desirable to develop an improved process for producing the above imidazole derivatives more easily and in higher yield.

DISCLOSURE OF INVENTION

From the above viewpoint, the present inventors have extensively studied to find out the ameliorated process of 4-(piperidin-4-ylalkyl)imidazole derivatives, and they have found that the use of specific imidazole alkylphosphonate esters could lead to the really easy and high-yielded production of the desired imidazole derivatives. Based upon the new findings, the present invention has been completed.

BEST MODE FOR CARRYING OUT THE INVENTION

Thus, the present invention provides novel imidazole alkylphosphonates of the following general formula (I):

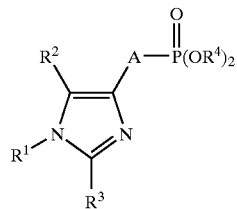

(I)

wherein:
$R^1$ is an amino-protecting group;
$R^2$ and $R^3$ are the same or different and are each a hydrogen atom, a lower alkyl group, or a hydroxy-(lower alkyl) group;
$R^4$ is a lower alkyl group, a halogenated lower alkyl group, or a substituted or unsubstituted phenyl group; and
A is an optionally substituted straight chain alkylene group having 1–3 carbon atoms,
which are useful as an intermediate for the production of imidazole derivatives.

Further, the present invention provides the improvement in the production of imidazole derivatives of the following general formula (VI):

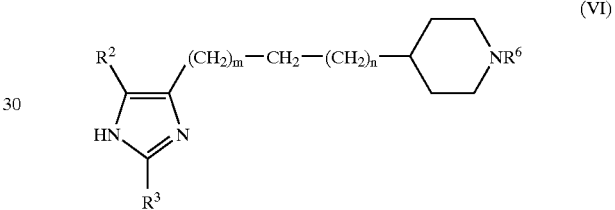

(VI)

wherein:
$R^2$ and $R^3$ are as defined above;
$R^6$ is a hydrogen atom or a lower alkyl group;
m is an integer of 1–3; and
n is an integer of 0–3; or
the following general formula (IX):

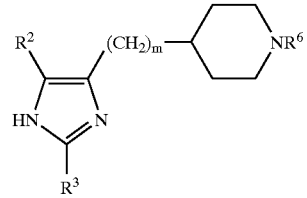

(IX)

wherein $R^2$, $R^3$, $R^6$, and m are as defined above, which are useful as positive control reagents for histamine $H_3$ agonists or antagonists, using said imidazole alkylphosphonate (I).

The amino-protecting groups of $R^1$ and $R^5$ as used herein are the same or different, and include for example, trityl, benzenesulfonyl, p-methoxyphenylsulfonyl, p-toluenesulfonyl, benzyl, p-methoxybenzyl, diphenylmethyl, benzyloxymethyl, 2,2,2-trichlorooxycarbonyl, tert-butyloxy-carbonyl, and the like.

The lower alkyl groups of $R^2$, $R^3$, $R^4$, $R^5$, and $R^6$ are the same or different and are straight chain or branched chain alkyl groups of 1–5 carbon atoms, such as methyl, ethyl, n-propyl, isopropyl, n-butyl, isobutyl, sec-butyl, tert-butyl, n-pentyl, isopentyl, neopentyl, tert-pentyl, and the like.

The hydroxy-(lower alkyl) groups of $R^2$ and $R^3$ are the same or different and are the above lower alkyl groups substituted with 1–2 hydroxy groups, such as hydroxymethyl, 2-hydroxyethyl, 3-hydroxypropyl, 4-hydroxybutyl, 5-hydroxypentyl, 1,2-dihydroxyethyl, 1,2-dihydroxypropyl, and the like.

The halogenated lower alkyl group of $R^4$ is the above lower alkyl group substituted with 1–5 halogen atoms, such as chlorine, bromine, and fluorine, and includes for example, chloromethyl, 2-chloroethyl, 2,2,2-trichloroethyl, bromomethyl, bromoethyl, 2,2,2-tribromoethyl, fluoromethyl, 2-fluoroethyl, 2,2,2-trifluoroethyl, pentafluoroethyl, and the like.

The substituted or unsubstituted phenyl group of $R^4$ includes phenyl groups having 1–3 substituents selected from the group consisting of a lower alkyl, a lower alkoxy, a halogen atom, hydroxy, trifluoromethyl, nitro, and amino on the phenyl ring.

The lower alkoxy group is a straight chain or branched chain alkoxy group having 1–5 carbon atoms, such as methoxy, ethoxy, n-propoxy, isopropyloxy, n-butoxy, isobutyloxy, tert-butyloxy, n-pentyloxy, and the like.

The halogen atoms include fluorine, bromine, chlorine, iodine, and the like.

The optionally substituted straight chain alkylene group having 1–3 carbon atoms of "A" denotes an alkylene group optionally substituted with a lower alkyl group or a hydroxy-(lower alkyl) group, such as methylmethylene, methylethylene, ethylmethylene, hydroxymethylmethylene, hydroxymethylethylene, hydroxyethylmethylene and the like.

Preferred imidazole alkylphosphonates (I) of the present invention are the compounds wherein $R^1$ is trityl, benzyl, benzyloxymethyl, or tert-butyloxycarbonyl; $R^2$ is a hydrogen atom, methyl, or ethyl; $R^3$ is a hydrogen atom, methyl, or ethyl; $R^4$ is a lower alkyl, phenyl, 2,2,2-trifluoroethyl; A is a substituted or unsubstituted $C_1$–$C_3$ alkyl, more preferably, $R^1$ is trityl, $R^2$ is a hydrogen atom, $R^3$ is a hydrogen atom, $R^4$ is ethyl, and A is methylene or methylmethylene.

The imidazole alkylphosphonates (I) of the present invention can be prepared, for example, the method of the following Scheme 1 (hereinafter referred to as Method A).

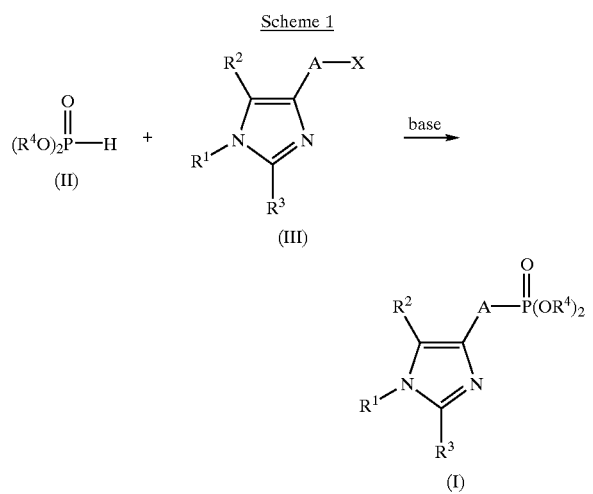

wherein $R^1$, $R^2$, $R^3$, $R^4$, and A are as defined above; X means a halogen atom, a methanesulfonyloxy group, or a p-toluenesulfonyloxy group.

The phosphonate derivatives (II) and the imidazole derivatives (III) are reacted in the presence of a base in an appropriate solvent to give the desired imidazole alkylphosphonates (I).

The organic solvent as used above includes tetrahydrofuran, acetonitrile, benzene, chlorobenzene, cyclohexane, diethyl ether, diisopropyl ether, N,N-dimethylformamide, dimethylsulfoxide, 1,4-dioxane, ethyleneglycol monoethyl ether, n-hexane, nitrobenzene, n-pentane, pyridine, toluene, xylene, and so on.

The base includes lithium bis(trimethylsilyl)amide, n-butyllithium, sec-butyllithium, tert-butyllithium, phenyllithium, ethyllithium, sodium amide, potassium amide, methylsulfinyl carbanion, sodium bis(trimethylsilyl)amide, potassium bis(trimethylsilyl)amide, lithium diisopropylamide amide, alkyl magnesium reagent (Grignard reagent), amidine base typified by 1,8-diazabicyclo[5,4,0]-7-undecene (DBU), and so on.

The above reaction is carried out at the initial reactive temperature of −78° C. to −20° C., and then heated to room temperature to about reflux temperature of the organic solvent (about 70° C.). The compound (II) and the compound (III) are used in the ratio of equimolar to 3:1 (mole ratio; hereinafter defined the same). Suitable examples of the compound (III) are (1-triphenylmethylimidazol-4-yl)-methyl chloride, (1-triphenylmethylimidazol-4-yl)methyl bromide, (1-triphenylmethylimidazol-4-yl)methyl iodide, (1-triphenylmethylimidazol-4-yl)methyl methanesulfonate, (1-triphenylmethylimidazol-4-yl)methyl p-toluenesulfonate, and the like.

Alternatively, the imidazole alkylphosphonates (I) may also be produced by the method of the following Scheme 2 (hereinafter referred to as Method B).

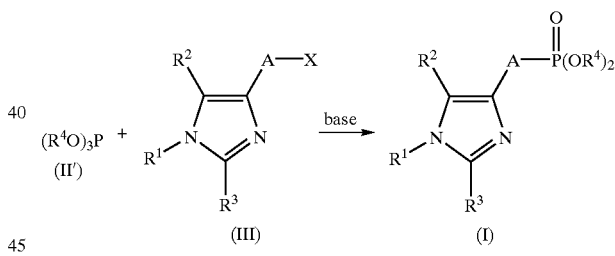

wherein $R^1$, $R^2$, $R^3$, $R^4$, A and X are as defined above.

The trialkylphosphite (II') and the imidazole derivative (III) are reacted in an appropriate solvent such as N,N-dimethylformamide or without any solvent to give the imidazole alkylphosphonate (I).

The above reaction is completed in a very short time of several tens of seconds to several minutes under microwaves. The solvent which can be used in the above reaction is for example N,N-dimethylformamide, dimethylsulfoxide, ethylene glycol, ethanol, benzene, toluene, xylene, chlorobenzene, 1,2-dichlorobenzene, tetrahydrofuran, dioxane, and the like.

Next, the preparation of the imidazole derivatives of the general formula (VI) or (IX) using the imidazole alkylphosphonate (I) of the present invention can be carried out by the following methods.

The imidazole derivatives of the general formula (VI) can be prepared by the method of the following Scheme 3.

Scheme 3

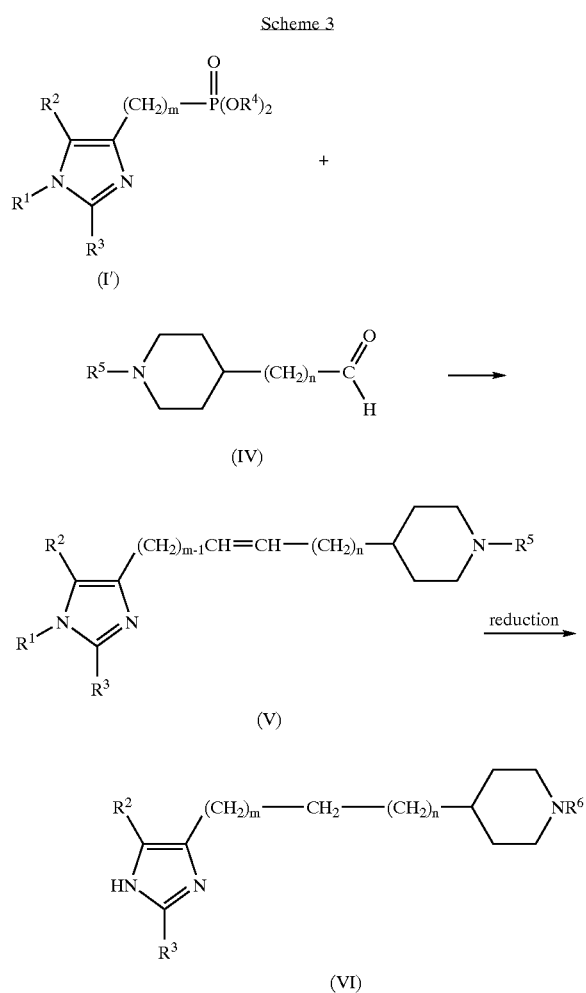

wherein $R^1$, $R^2$, $R^3$, $R^4$, $R^6$, m and n are as defined above, and $R^5$ is an amino-protecting group or a lower alkyl group.

The reaction of the imidazole alkylphosphonate (I') with the piperidine compound (IV) is carried out in the presence of a base in an aprotic solvent at the temperature of 0° C. to about boiling point of the solvent.

The aprotic solvent as used above includes N,N-dimethylformamide; aromatic hydrocarbons such as benzene, toluene, xylene, and the like; ethers such as tetrahydrofuran, diethyl ether, diisopropyl ether, 1,4-dioxane, ethylene glycol monoethyl ether and the like; aliphatic and alicyclic hydrocarbons such as cyclohexane, n-hexane, n-pentane and the like; substituted aromatic hydrocarbons such as chlorobenzene, nitrobenzene and the like; dimethylsulfoxide and so on.

The base includes potassium tert-butoxide; alkyllithiums such as n-butyllithium, sec-butyllithium, tert-butyllithium, phenyllithium, ethyllithium, and the like; alkali metal amides such as sodium amide, potassium amide, and the like; methylsulfinyl carbanion; sodium bis-(trimethylsilyl)amide; potassium bis(trimethylsilyl)amide; lithium diisopropylamide; alkyl magnesium reagents (Grignard reagents); and so on.

The compound (I') and the compound (IV) in the above reaction are generally used in the ratio of equimolar to 3:1 (compound (I'): compound (IV)).

The compound (V) thus obtained is converted into the desired imidazole derivative (VI) by catalytic reduction in a usual manner.

The catalytic reduction is carried out with the known catalyst for catalytic reduction such as palladium, nickel, platinum, rhodium, ruthenium, and the like, in a solvent such as water, methanol, ethanol, acetic acid, ethyl acetate, and the like, under the hydrogen pressure of about 1 atm to about 3.5 kg/cm$^2$, which will be completed in several tens of minutes to several hours.

The imidazole derivatives of the general formula (IX) can be prepared by the method of the following Scheme 4.

Scheme 4

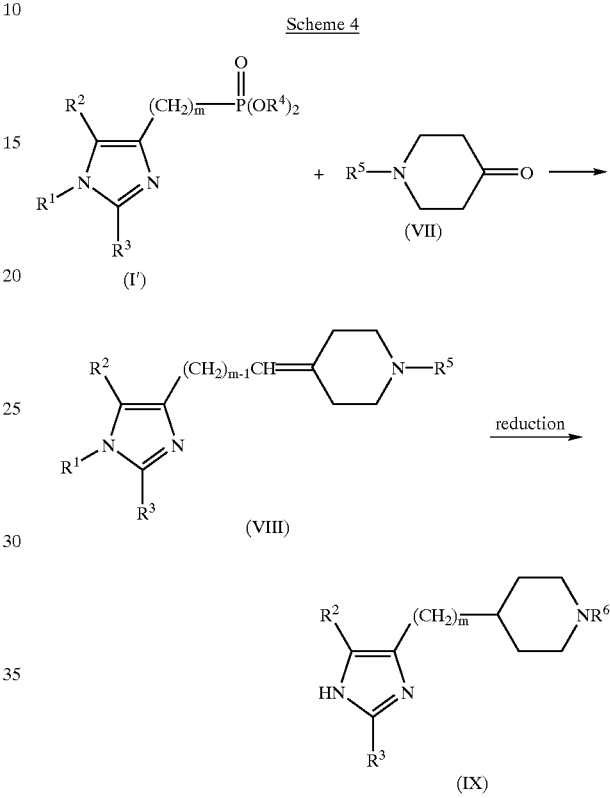

wherein $R^1$, $R^2$, $R^3$, $R^4$, $R^5$, $R^6$, and m are as defined above.

The reaction of the above imidazole alkylphosphonate (I') and the piperidone compound (VII) can be carried out under the same condition as the above-mentioned Scheme 3 as to the reaction of the compound (I') and the compound (IV).

The compound (VIII) can be also reduced to the desired imidazole derivative (IX) under the same condition as in the conversion of the compound (V) to the compound (VI) as shown in the above-mentioned Scheme 3.

The compounds obtained in the above reactions can be purified by the conventional methods such as recrystallization, chromatography, and so on.

Further, when the product is given in the form of a salt such as acid addition salt, the salt may be converted into the free base thereof by treating it with a base, reversely the free base may be also converted into the pharmaceutically acceptable acid addition salt. The pharmaceutically acceptable salts are, for example salts with inorganic acids such as hydrochloric acid, sulfuric acid, perchloric acid, nitric acid, hydrobromic acid, phosphoric acid, and the like; and salts with organic acids such as acetic acid, malic acid, citric acid, oxalic acid, maleic acid, fumaric acid, benzoic acid, and the like.

The following Examples illustrate embodiments of the present invention and should not be construed to be limited thereto.

EXAMPLE 1

Preparation of diethyl(1-triphenylmethylimidazol-4-yl)-methylphosphonate (Method A)

To a solution of diethylphosphite (4.30 g, 31.2 mmol) in dry tetrahydrofuran (hereinafter abbreviated to THF) (10 ml) was added 1M THF solution of lithium bis-(trimethylsilyl) amide (31.2 ml, 31.2 mmol) dropwise over 1 hour at −72° C. under argon flow, followed by adding dropwise (1-triphenylmethylimidazol-4-yl)methyl chloride (9.30 g, 26.0 mmol) in THF (80 ml) over 30 minutes. The reaction mixture was stirred for 15 minutes at the same temperature, and then was heated to room temperature and stirred for additional 3 hours at room temperature. After the reaction was quenched by addition of saturated aqueous ammonium chloride (150 ml), the THF was removed and the residue was extracted four times with ethyl acetate (100 ml). The organic layers were dried over anhydrous sodium sulfate, and then concentrated under reduced pressure. The obtained crude pale yellow solid product was purified by chromatography on silica gel column using methanol-ethyl acetate (1:20) to give diethyl(1-triphenylmethylimidazol-4-yl) methylphosphonate (10.30 g, 86%) as a white powder. This powder was recrystallized from a mixture of ethyl acetate and hexane to provide the titled compound as white small needles (m.p. 141–144° C.).

$^1$H NMR (CDCl$_3$) δ 1.24 (t, J=8.0 Hz, 6H), 3.17 (d, J=21.6 Hz, 2H), 4.02 (quint, J=6.0 Hz, 4H), 6.81 (s, 1H), 7.10–7.40 (m, 16H). $^{31}$P NMR (CDCl$_3$) δ 27.0 (s). SIMS m/z: 460 (M$^+$), HR-MS m/z: 460.1898 (calcd for C$_{27}$H$_{29}$N$_2$O$_3$P: 460.1914). Anal Calcd for C$_{27}$H$_{29}$N$_2$O$_3$P: C, 86.08; H, 7.22; N, 6.69. Found: C, 86.03; H, 7.32; N, 6.41.

(Method B)

To (1-triphenylmethylimidazol-4-yl)methyl chloride (359 mg, 1.00 mmol) was added a solution of triethylphosphite (249 mg, 1.50 mmol) in N,N-dimethylformamide (1 ml), and then the reaction mixture was stirred at 80° C. for 16 hours under argon flow. The reaction mixture was distilled under reduced pressure to give a white residue. Purification of this residue through chromatography on silica gel column using methanol-ethyl acetate (1:20) provided the titled compound (65 mg, 14%) as a white powder.

EXAMPLE 2

Preparation of 1-benzyl-4-(1-triphenylmethylimidazol-4-ylmethylene)piperidine

To a solution of commercially available 1-benzyl-4-piperidone (95 mg, 0.5 mmol) in THF (6 ml) were added the compound obtained in the above Example 1 (276 mg, 0.6 mmol) and potassium tert-butoxide (67 mg, 0.6 mmol), and then the reaction mixture was refluxed under argon flow for 1.5 hours. Saturated aqueous sodium chloride (1 ml) was added and then the solvent was evaporated under reduced pressure. To the residue was added saturated aqueous sodium chloride (10 ml), the solution was extracted 3 times with chloroform (20 ml). The extracts were dried over anhydrous magnesium sulfate, and the solvent was removed under reduced pressure. Purification of the yellow oil obtained through chromatography on silica gel column using ethyl acetate provided the titled compound (246 mg, 99%) as a colorless viscous substance.

$^1$H NMR (CDCl$_3$) δ 2.30–2.40 (m, 2H), 2.42–2.60 (m, 4H), 2.79–2.90 (m, 2H), 3.52 (s, 2H), 6.02 (s, 1H), 6.66 (s, 2H) 7.08–7.44 (m, 2H). EIMS m/z: 495 (M$^+$), HR-MS m/z: 495.2681 (calcd for C$_{35}$H$_{33}$N$_3$: 495.2673).

EXAMPLE 3

Preparation of 4-(1H-imidazol-4-ylmethyl) piperidine dihydrochloride(immepip dihydrochloride)

To a solution of the compound obtained in the above Example 2 (162 mg, 0.327 mmol) in ethanol (5 ml) was added 1N hydrochloric acid (1.5 ml, 5 eq), and the reaction mixture was stirred at room temperature for 10 minutes and then the solvent was removed under reduced pressure. The residue was dissolved in methanol (20 ml), 10% palladium-carbon (120 mg) was added, and then catalytic reduction was carried out at 3.0 Kg/cm$^2$ for 15 hours. The catalyst was filtered off, and the filtrate was concentrated under reduced pressure. The resultant residue was dissolved in water (20 ml), washed 3 times with benzene (20 ml), and then the aqueous layer was concentrated under reduced pressure to give the titled compound, immepip dihydrochloride (84 mg, quantitative) as a white powder (m.p. 235–239° C.).

$^1$H NMR (500 MHz) (CD$_3$OD) δ 1.52 (m, 2H), 1.92 (dm, J=13.0 Hz, 2H), 2.02 (m, 1H), 2.77 (d, J=7.0 Hz, 2H), 3.01 (tm, J=13.0 Hz, 2H), 3.41 (dm, J=13.0 Hz, 2H), 7.42 (s, 1H), 8.85 (s, 1H). $^{13}$C NMR (CD$_3$OD) δ 29.4, 31.4, 34.7, 45.0, 118.0, 132.7, 135.0. EIMS m/z: 165 (M$^+$), HR-MS m/z: 165.1263 (calcd for C$_9$H$_{15}$N$_3$: 165.1265).

EXAMPLE 4

Preparation of 4-(1H-imidazol-4-ylmethyl) piperidine (immepip)

Immepip dihydrochloride of the above Example 3 was dissolved in methanol, a small amount of silica gel was added thereto, and immepip dihydrochloride was coated onto the silica gel for the mean time. Said silica gel was placed onto a basic silica gel column, and elution with a mixture of chloroform-methanol-28% aqueous ammonia (50:2:1) provided the titled compound, immepip (48 mg) as a colorless oil.

$^1$H NMR (CD$_3$OD) δ 1.10 (qd, J=13.0 Hz, 5.0 Hz, 2H), 1.63 (dm, J=13.0 Hz, 3H), 2.49 (tm, J=13.0 Hz, 4H), 2.95 (dm, J=13.0 Hz, 2H), 6.67 (s, 1H), 7.46 (s, 1H).

EXAMPLE 5

Preparation of 4-(1H-imidazol-4-ylmethyl) piperidine dihydrobromide

To the product of Example 4 (48 mg) was added 50% aqueous HBr (240 mg, 5 eq), the solution was stirred in ethanol (20 ml) for 15 minutes, and concentrated under reduced pressure. The residue was washed four times with acetone (3 ml) to give immepip dihydrobromide (95 mg, quantitative) as a white powder (m.p. 237–239° C.).

$^1$H NMR (D$_2$O) δ 1.46 (qd, J=13.0 Hz, 5.0 Hz, 2H), 1.92 (dm, J=13.0 Hz, 2H), 1.99 (m, 1H), 2.75 (d, J=7.0 Hz, 2H), 2.99 (tm, J=13.0 Hz, 2H), 3.43 (dm, J=13.0 Hz, 2H), 7.28 (s, 1H), 8.59 (s, 1H). $^{13}$C NMR(D$_2$O) δ 29.2, 31.3, 34.4, 45.3, 117.8, 132.4, 134.5. Anal Calcd for C$_9$H$_{15}$N$_3$.2HBr: C, 33.05; H, 5.24; N, 12.85. Found: C, 32.80; H, 5.24; N, 12.70.

EXAMPLE 6

Preparation of (E)-1-benzyl-4-(1-triphenylmethylimidazol-4-ylethylene)piperidine To a solution of 1-benzyl-4-formylpiperidine (244 mg, 1.2 mmol) in THF (10 ml) were added diethyl(1- triphenylmethylimidazol-4-yl)methylphosphonate (460 mg, 1.0 mmol) and potassium tert-butoxide (112 mg, 1.0 mmol) and the reaction mixture was refluxed under argon flow for 2 hours. The reaction was quenched with water (1 ml) and the THF was removed under reduced pressure. To the resultant residue was added saturated sodium chloride (40 ml). The whole was extracted four times with ethyl acetate (40 ml), dried over anhydrous magnesium sulfate, and concentrated under reduced pressure. The resultant yellow oil was chromatographed on silica gel column using ethyl acetate to provided the title compound (377 mg, 74%) as a colorless viscous material.

$^1$H NMR (CDCl$_3$) δ 1.56 (qd, J=15.0 Hz, 4.4 Hz, 2H), 1.66–1.78 (dm, J=15.0 Hz, 2H), 1.92–2.23 (m, 3H), 2.88–2.94 (dm, J=15.0 Hz, 2H), 3.49 (s, 2H), 6.19 (d, J=15.5 Hz, 1H), 6.32 (dd, J=15.5 Hz, 6.7 Hz, 1H), 6.68 (s, 1H), 7.05–7.40 (m, 21H). EIMS m/z: 509 (M$^+$), HR-MS m/z: 509.2827 (calcd for C$_{36}$H$_{35}$N$_3$: 509.2829).

EXAMPLE 7

Preparation of 4-(1H-imidazol-4-ylethyl)piperidine (VUF4929)

To a solution of the compound obtained in the above Example 6 (196 mg, 0.385 mmol) in ethanol (5 ml) was added 1N hydrochloric acid (2.0 ml, 5 eq). The reaction mixture was stirred at room temperature for 10 minutes, and then the solvent was removed under reduced pressure. The residue was dissolved in methanol (20 ml), and thereto 10% palladium-carbon (200 mg) was added, and catalytic reduction was carried out at 3.5 Kg/cm$^2$ for 14 hours. The catalyst was filtered off, and the filtrate was concentrated under reduced pressure. The resultant residue was dissolved in water (20 ml), washed 3 times with benzene (20 ml), and then the aqueous layer was concentrated under reduced pressure to give the crude product as a white solid. This compound was purified through chromatography on silica gel column using chloroform-methanol-28% aqueous ammonia (10:20:1) to give the titled compound, VUF4929 (68 mg, 99%) as a colorless oil.

$^1$H NMR (CD$_3$OD) δ 1.19 (qd, J=13.0 Hz, 3.5 Hz, 2H), 1.36–1.52 (m, 1H), 1.60 (q, J=7.2 Hz, 2H), 1.70–1.82 (dm, J=13.0 Hz, 2H), 2.50–2.70 (m, 4H), 3.00–3.10 (dm, J=13.0 Hz, 2H), 6.78 (s, 1H), 7.59 (s, 1H). EIMS m/z: 179 (M$^+$), HR-MS m/z: 179.1424 (calcd for C$_{10}$H$_{17}$N$_3$: 179.1422).

To a solution of the compound (68 mg, 0.380 mmol) obtained above in ethanol (5 ml) was added 1N hydrochloric acid (2.0 ml, 5 eq). The reaction mixture was stirred at room temperature for 15 minutes, and concentrated under reduced pressure to provide the dihydrochloride salt (VUF4929 dihydrochloride) as a white powdery crystal (m.p. 216–220° C.).

$^1$H NMR (CD$_3$OD) δ 1.47 (qd, J=13.0 Hz, 3.5 Hz, 2H), 1.65–1.75 (m, 3H), 1.97–2.04 (dm, J=13.0 Hz, 2H), 2.80 (t, J=7.2 Hz, 2H), 3.00 (t, J=13.0 Hz, 2H), 3.37–3.43 (dm, J=13.0 Hz, 2H), 7.36 (s, 1H), 8.81 (s, 1H). $^{13}$C NMR (CD$_3$OD) δ 22.4, 29.7, 34.2, 35.6, 45.2, 116.8, 134.7, 135.3.

EXAMPLE 8

Preparation of bis(2,2,2-trifluoroethyl)(1-triphenylmethylimidazol-4-yl)methylphosphonate To a solution of bis(2,2,2-trifluoroethyl)phosphite (0.11 ml, 0.6 mmol) in THF (1.5 ml) were added 1,8-diazabicyclo[5,4,0]-7-undecene (DBU) (0.09 ml, 0.6 mmol) and (1-triphenylmethylimidazol-4-yl)methyl chloride (71.8 mg, 0.2 mmol). The reaction mixture was refluxed under argon flow for 22 hours. The solvent was removed under reduced pressure, and water (10 ml) was added to the residue, which was then extracted 3 times with ethyl acetate (10 ml). The resultant organic layers were washed with saturated brine, dried over anhydrous sodium sulfate, and the solvent was removed under reduced pressure. The obtained white solid was purified through chromatography on silica gel column using ethyl acetate-hexane (3:2) to give bis(2,2,2-trifluoroethyl)(1-triphenylmethylimidazol-4-yl) methylphosphonate (34 mg, 30%) as a white powder. This powder was recrystallized from a mixture of ethyl acetate and hexane to provide a white small needle crystal (m.p. 145–148° C.).

$^1$H NMR (CDCl$_3$) δ 3.34 (d, J=10.5 Hz, 2H), 4.30 (quint, d, J=3.9 Hz, 1.3 Hz, 4H), 6.80 (s, 1H), 7.08–7.50 (m, 16H) $^{31}$P NMR(CDCl$_3$) δ 29.9 (s). Anal Calcd for C$_{27}$H$_{23}$N$_2$O$_3$PF$_6$: C, 57.03; H, 4.08; N, 4.93. Found: C, 57.03; H, 4.19; N, 4.94.

EXAMPLE 9

Preparation of diethyl(1-triphenylmethylimidazol-5-methyl-4-yl)methylphosphonate To a solution of diethylphosphite (331 mg, 2.4 mmol) in THF (1 ml) was added 1M THF solution of lithium bis(trimethylsilyl)amide (2.4 ml, 2.4 mmol) dropwise over 15 minutes at −72° C. under argon flow, followed by adding dropwise 4-chloromethyl-5-methyl-1-triphenylmethylimidazole in THF (5 ml) over 20 minutes. After stirring at the same temperature for 20 minutes, the reaction mixture was heated to room temperature, and stirred at room temperature for additional 2.5 hours. The reaction was quenched with saturated aqueous ammonium chloride (1 ml), and then the residual THF was removed under reduced pressure. Water (30 ml) was added to the residue, and the mixture was extracted 3 times with ethyl acetate (30 ml). The organic layers were dried over anhydrous sodium sulfate, concentrated under reduced pressure to give an amorphous material, and the material was purified through chromatography on silica gel column using methanol-ethyl acetate (1:20) to provide the titled compound (270 mg, 30%) as a light yellow amorphous.

$^1$H NMR (CDCl$_3$) δ 1.29 (t, J=7.3 Hz, 6H), 1.45 (d, J=3.3 Hz, 3H), 3.12 (d, J=20.1 Hz, 2H), 4.08 (quint, J=7.3 Hz, 4H), 7.03–7.20 (m, 6H), 7.20–7.40 (m, 10H). EIMS m/z: 474 (M$^+$), HR-MS m/z: 474.2060 (calcd for C$_{28}$H$_{31}$N$_2$O$_3$P: 474.2071).

EXAMPLE 10

Preparation of diphenyl(1-triphenylmethylimidazol-4-yl)-methylphosphonate

To a solution of triphenylphosphite (140 mg, 0.6 mmol) in dry dichloromethane (1 ml) were added DBU (106 mg, 0.7 mmol) and (1-triphenylmethylimidazol-4-yl)methyl chloride (180 mg, 0.5 mmol). The reaction mixture was stirred at room temperature under argon flow for 25 hours. Water (1 ml) was added to the reaction mixture and then the solvent was removed. To the obtained residue was added saturated brine (20 ml), and the whole was extracted 3 times with ethyl acetate-hexane (3:1) (15 ml), dried over anhydrous sodium sulfate, and the solvent was removed under reduced pressure. The obtained white solid crude product was purified through chromatography on silica gel column using ethyl acetate-hexane (3:2) to provide the titled compound (81 mg, 29%) as a white powder (m.p. 128–136° C.).

$^1$H NMR (CDCl$_3$) δ 3.44 (d, J=21.8 Hz, 2H), 6.85 (s, 1H), 6.95–7.30 (m, 25H), 7.36 (s, 1H). SIMS m/z: 557 (M$^+$+1), HR-MS m/z: 557.1991 (calcd for C$_{35}$H$_{30}$N$_2$O$_3$P: 557.1992).

EXAMPLE 11

Preparation of diethyl 1-(1-triphenylmethylimidazol-4-yl)-ethylphosphonate

To a solution of diethyl(1-triphenylmethylimidazol-4-yl) methylphosphonate (690 mg, 1.5 mmol) in THF (20 ml) was added 1.6M hexane solution of n-butyllithium (0.94 ml, 1.5 mmol) dropwise over 10 minutes at −72° C. under argon flow, followed by adding a solution of methyl iodide (213 mg, 1.5 mmol) in THF (5 ml) dropwise over 10 minutes. After stirring at the same temperature for 30 minutes, the reaction mixture was heated to room temperature, and then stirred at room temperature for 2 hours. The reaction was quenched with water (1 ml), and then the THF was removed under reduced pressure. Saturated brine (40 ml) was added to the residue, and the mixture was extracted 3 times with ethyl acetate (40 ml). The resultant organic layers were dried over anhydrous sodium sulfate, and concentrated under reduced pressure to give the crude product as a light yellow solid. It was purified through chromatography on silica gel column using methanol-ethyl acetate (1:9) to provide the titled compound (690 mg, 97%) as a white powder (m.p. 124–126° C.). This powder was recrystallized from a mixture of ethyl acetate and hexane to provide the title compound as a small needle crystal (m.p. 125–128° C.).

$^1$H NMR (CDCl$_3$) δ 1.20 (t, J=7.3 Hz, 3H), 1.25 (t, J=7.3 Hz, 3H), 1.52 (dd, J=17.8 Hz, 7.5 Hz, 3H), 3.26 (dq, J=22.1 Hz, 7.5 Hz, 1H), 3.90–4.08 (m, 4H), 6.82 (s, 1H), 7.10–7.40 (m, 16H). $^{13}$C NMR (CDCl$_3$) δ 14.9, 16.4, 31.7, 32.8, 61.8, 62.0, 75.3, 119.3, 127.9, 130.0, 137.8, 137.9, 142.4. $^{31}$P NMR (CDCl$_3$) δ 30.27. SIMS m/z: 474 (M$^+$), HR-MS m/z: 474.2062 (calcd for C$_{28}$H$_{31}$N$_2$O$_3$P: 474.2071). Anal Calcd for C$_{28}$H$_{31}$N$_2$O$_3$P: C, 70.87; H, 6.58; N, 5.90. Found: C, 70.90; H, 6.68; N, 5.94.

INDUSTRIAL APPLICABILITY

The present invention provides imidazole alkylphosphonates (I) useful as an intermediate for producing imidazole derivatives that are known as histamine H$_3$ agonists and antagonists, and from said intermediates the imidazole derivatives useful as histamine H$_3$ ligands may be so easily prepared in high yield.

What is claimed is:

1. An imidazole alkylphosphonate of the general formula (I):

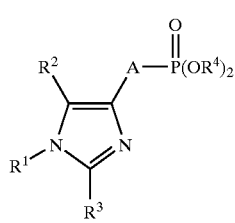

wherein;
R$^1$ is an amino-protecting group;
R$^2$ and R$^3$ are the same or different and are each a hydrogen atom, a lower alkyl group, or a hydroxy-(lower alkyl) group;
R$^4$ is a lower alkyl group, a halogenated lower alkyl group, or a substituted or unsubstituted phenyl group; and
A is an optionally substituted straight chain alkylene group having 1–3 carbon atoms.

2. A method for the preparation of an imidazole alkylphosphonate of the general formula (I) in claim 1, characterized by reacting a phosphonate derivative of the general formula (II):

wherein R$^4$ is as defined in claim 1, with an imidazole derivative of the general formula (III):

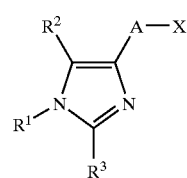

wherein;
X is a halogen atom, a methanesulfonyloxy group, or a p-toluenesulfonyloxy group; and
R$^1$, R$^2$, R$^3$, and A are as defined in claim 1, in the presence of a base.

3. A method for the preparation of an imidazole derivative of the general formula (VI):

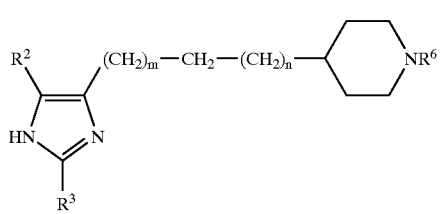

wherein;
R$^2$ and R$^3$ are as defined in claim 1;
m is an integer of 1–3;
n is an integer of 0–3; and
R$^6$ is a hydrogen atom or a lower alkyl group, characterized by reacting an imidazole alkylphosphonate of the general formula (I'):

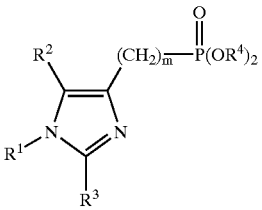

wherein;
R$^1$, R$^2$, R$^3$, and R$^4$ are as defined in claim 1; and
m is as defined above, with a piperidine compound of the general formula (IV):

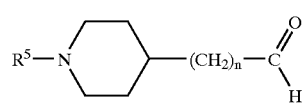

wherein;
R$^5$ is an amino-protecting group or a lower alkyl group; and n is as defined above, to give a compound of the formula (V):

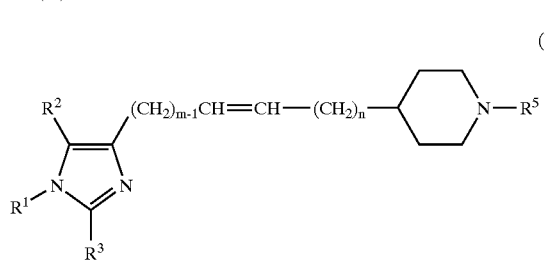
(V)

wherein;

$R^1$, $R^2$, and $R^3$ are as defined in claim 1; and m, $R^5$, and n are as defined above, and then reducing said compound.

4. A method for the preparation of an imidazole derivative of the general formula (IX):

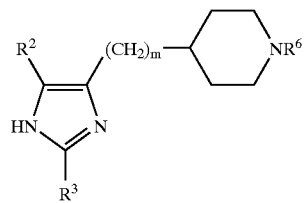
(IX)

wherein;

$R^2$ and $R^3$ are as defined in claim 1;

m is an integer of 1–3;

$R^6$ is a hydrogen atom or a lower alkyl group, characterized by reacting an imidazole alkylphosphonate of the general formula (I'):

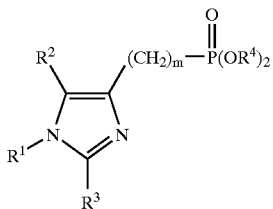
(I')

wherein;

$R^1$, $R^2$, $R^3$, and $R^4$ are as defined in claim 1; and m is as defined above, with a piperidone compound of the general formula (VII):

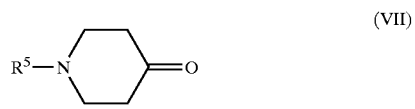
(VII)

wherein $R^5$ is an amino-protecting group or a lower alkyl group, to give a compound of the formula (VIII):

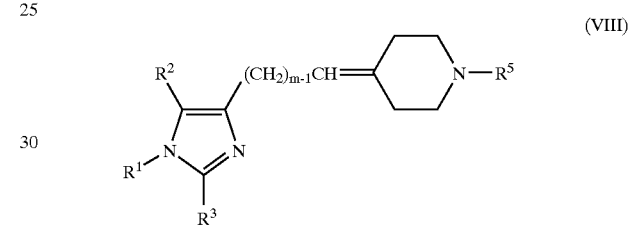
(VIII)

wherein;

$R^1$, $R^2$, and $R^3$ are as defined in claim 1; and m and $R^5$ are as defined above, and then reducing said compound.

* * * * *